(12) United States Patent
Dumont et al.

(10) Patent No.: US 8,938,286 B2
(45) Date of Patent: Jan. 20, 2015

(54) ACTIVE IMPLANTABLE MEDICAL DEVICE COMPRISING MEANS FOR THE DIAGNOSIS OF HEART FAILURE

(71) Applicant: Sorin CRM SAS, Clamart Cedex (FR)

(72) Inventors: Jérôme Dumont, Chatillon (FR); Lionel Giorgis, Saint Brieuc (FR)

(73) Assignee: Sorin CRM SAS, Clamart (FR)

( * ) Notice: Subject to any disclaimer, the term of this patent is extended or adjusted under 35 U.S.C. 154(b) by 0 days.

(21) Appl. No.: 13/755,519

(22) Filed: Jan. 31, 2013

(65) Prior Publication Data

US 2013/0197378 A1 Aug. 1, 2013

(30) Foreign Application Priority Data

Jan. 31, 2012 (FR) ...................................... 12 50922

(51) Int. Cl.
| | |
|---|---|
| *A61B 5/0452* | (2006.01) |
| *A61B 5/02* | (2006.01) |
| *A61B 5/0402* | (2006.01) |
| *A61B 5/0205* | (2006.01) |
| *A61B 5/00* | (2006.01) |

(52) U.S. Cl.
CPC ................. *A61B 5/02* (2013.01); *A61B 5/0402* (2013.01); *A61B 5/0205* (2013.01); *A61B 5/0452* (2013.01); *A61B 5/7275* (2013.01); *A61B 5/7221* (2013.01)
USPC .......................................... 600/509; 600/508

(58) Field of Classification Search
USPC ......................................................... 600/509
See application file for complete search history.

(56) References Cited

U.S. PATENT DOCUMENTS 5,411,031 A * 5/1995 Yomtov ......................... 600/519
6,221,011 B1 * 4/2001 Bardy ............................ 600/300

(Continued)

FOREIGN PATENT DOCUMENTS

| EP | 0 570 896 | 11/1993 |
|---|---|---|
| EP | 0 966 987 | 12/1999 |

(Continued)

OTHER PUBLICATIONS

Preliminary Search Report for French Patent Application No. 1250922, dated Sep. 20, 2012, 2 pages.

*Primary Examiner* — Michael Kahelin

(74) *Attorney, Agent, or Firm* — Foley & Lardner LLP

(57) ABSTRACT

Methods, devices, and processor-readable storage media are provided for the diagnosis of heart failure. A method in this context includes collecting, using an implantable device, reference episodes, the reference episodes comprising, at least one of: electrical activity signals of a myocardium; myocardium hemodynamic activity signals, or indicators reflecting variation of physical parameters, variation of activity, and variation of hemodynamic phases between phases of effort and phases of recovery; generating an in-suspicion model-cycle and an off-suspicion model-cycle based on the reference episodes; and determining whether to generate an early heart failure alert, based on a difference between the in-suspicion model-cycle and the off-suspicion model-cycle.

20 Claims, 5 Drawing Sheets

(56) References Cited

U.S. PATENT DOCUMENTS

| | | |
|---|---|---|
| 6,246,910 B1 | 6/2001 | Bonnet et al. |
| 7,570,990 B2 | 8/2009 | Faber et al. |
| 2007/0073350 A1 | 3/2007 | Casset |
| 2007/0150016 A1 | 6/2007 | Casset |
| 2007/0293736 A1 | 12/2007 | Casset |
| 2011/0009758 A1* | 1/2011 | Richardson .................. 600/509 |
| 2011/0118804 A1 | 5/2011 | Henry et al. |
| 2011/0166472 A1 | 7/2011 | Bjorling et al. |

FOREIGN PATENT DOCUMENTS

| | | |
|---|---|---|
| EP | 1 767 244 | 3/2007 |
| EP | 1 790 382 | 5/2007 |
| EP | 1 867 360 | 12/2007 |
| EP | 2 324 885 A1 | 5/2011 |
| WO | WO-2006/105143 | 10/2006 |
| WO | WO-2011/005373 | 1/2011 |
| WO | WO-2011/005376 | 1/2011 |

* cited by examiner

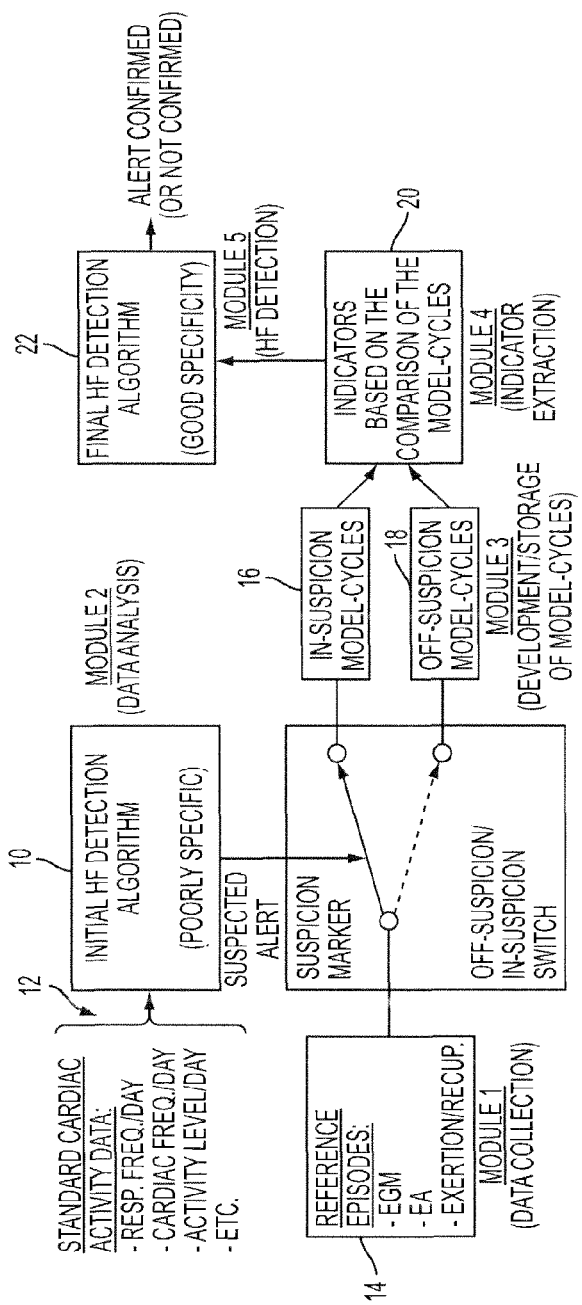
FIG. 1
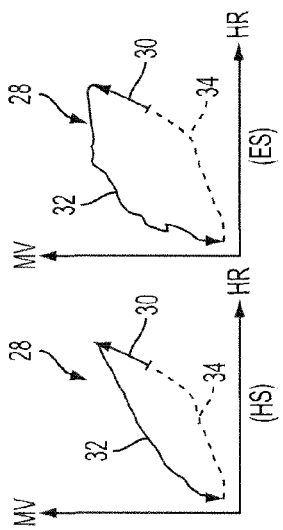
FIG. 2
FIG. 3
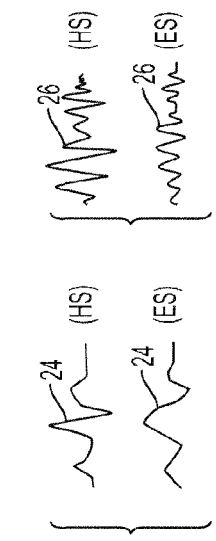
FIG. 4

US 8,938,286 B2

ACTIVE IMPLANTABLE MEDICAL DEVICE COMPRISING MEANS FOR THE DIAGNOSIS OF HEART FAILURE

CROSS-REFERENCE TO RELATED PATENT APPLICATIONS

This application claims priority from France Priority Application 1250922, filed Jan. 31, 2012, which is incorporated herein by reference in its entirety.

FIELD OF THE INVENTION

The invention relates to "active implantable medical devices" as defined by the Directive 90/385/EEC of 20 Jun. 1990 of the European Communities Council. In particular, it relates to devices for cardiac pacing, resynchronization, and/or defibrillation for diagnostics and treatment of cardiac arrhythmias, including active implants for pure diagnostic purpose.

More specifically, the invention concerns the preventive diagnosis of cardiac decompensation risk through analysis of signals collected by the implanted device. This diagnosis may be particularly useful with implants implementing resynchronization functions.

SUMMARY OF THE INVENTION

One embodiment relates to a method of diagnosis of heart failure. The method includes collecting data, using an implantable device. The data includes reference episodes (or data related to reference episodes). The reference episodes include at least one of: electrical activity signals of a myocardium; myocardium hemodynamic activity signals, or indicators reflecting variation of physical parameters, variation of activity, and variation of hemodynamic phases between phases of effort and phases of recovery. The method further includes generating an in-suspicion model-cycle and an off-suspicion model-cycle based on the reference episodes; and determining whether to generate an early heart failure alert, based on a difference between the in-suspicion model-cycle and the off-suspicion model-cycle.

In some embodiments of the method, the in-suspicion model-cycle or off-suspicion model-cycle includes at least one endocardial electrogram beat recorded during an episode fulfilling predetermined conditions of heart rate and patient activity. In some embodiments, the in-suspicion model-cycle or off-suspicion model-cycle includes at least one beat of an endocardiac acceleration signal recorded during an episode fulfilling predetermined conditions of heart rate and patient activity. According to some embodiments, the in-suspicion model-cycle or off-suspicion model-cycle includes at least one minute ventilation versus heart-rate characteristic pattern that was recorded during an episode comprising an effort phase followed by a recovery phase of the patient.

Some further embodiments of the method include updating the in-suspicion model-cycle and off-suspicion model-cycle; and storing the updated in-suspicion model-cycle and updated off-suspicion model-cycle. In some further embodiments, each of the in-suspicion model-cycle and the off-suspicion model-cycle is a combination of a previous model-cycle with at least one older model-cycle.

According to some embodiments of the method, generating the early heart failure alert includes generating at least one index of a clinical condition of a patient, based on the difference between the in-suspicion model-cycle and the off-suspicion model-cycle; and generating an early heart failure alert based on the at least one index. In some further embodiments, the at least one index of a clinical condition is updated periodically. In some further embodiments, the at least one index is calculated based on an average of model-cycles.

Another embodiment of the disclosure relates to a device for the diagnosis of heart failure. The device includes a processor, configured to execute steps of an embodiment of the method described above. The device may be a pacing, resynchronization, or defibrillation device or an implant for diagnostic purposes.

Yet another embodiment relates to a processor-readable, non-transitory storage medium having instructions stored thereon that, when executed by a processor, cause the processor to execute steps of an embodiment of the method described above.

BRIEF DESCRIPTION OF THE DRAWINGS

Further features, characteristics, and advantages of the present invention will become apparent to a person of skilled in the art from the following detailed description of preferred embodiments of the invention, made with reference to the annexed drawings, in which like reference characters refer to like elements and in which:

FIG. 1 is a block diagram that illustrates the general principle of the invention, with the various involved functional modules, according to an exemplary embodiment;

FIG. 2 is a diagram of a model-cycle of a signal including an electrogram (EGM) beat in a off-suspicion situation and in an in-suspicion situation, according to an exemplary embodiment;

FIG. 3 is a diagram of a model-cycle of a signal including an endocardial acceleration (EA) wave in an off-suspicion situation and in an in-suspicion situation, according to an exemplary embodiment;

FIG. 4 is a diagram illustrating a model-cycle of a signal including a cycle corresponding to the trace of the minute ventilation (MV) as a function of heart rate (HR) during a recovery phase following a stress phase, according to an exemplary embodiment;

DETAILED DESCRIPTION

Figure 5:
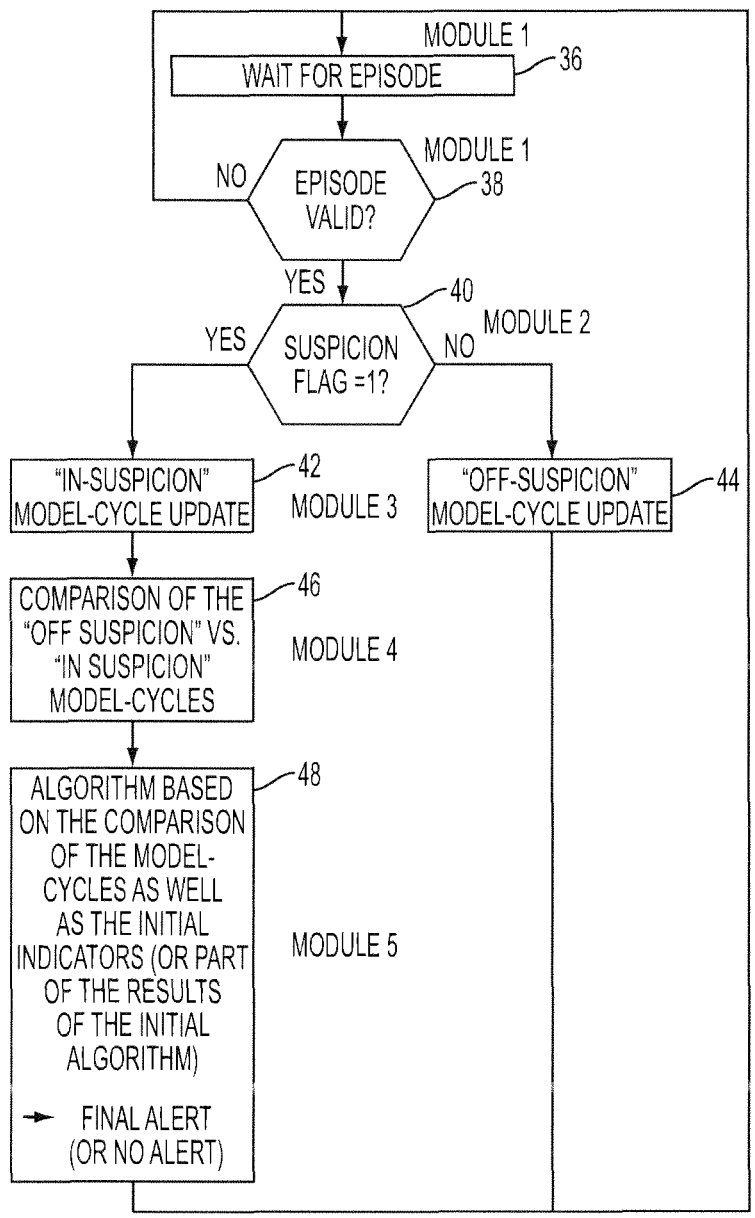
FIG. 5 is a flowchart describing successive actions performed when new valid data may be used to update the model-cycles and to produce a more reliable alert than the initial warning, according to an exemplary embodiment.

With general reference to the drawings, devices, methods, and storage media for diagnosis of heart failure are provided that are illustrated by embodiments described below. These may be implemented through the use of implanted devices, which, according to various embodiments, collect signals which aid in determining whether to generate an early heart failure alert.

According to various embodiments, signals collected by implanted devices may be of varied nature, whether signals from electrodes collecting the myocardium depolarization wave, measurements reflecting hemodynamic parameters, or signals delivered by physical sensors giving an indication of the activity level of the patient.

Methods of analyzing these signals may involve analysis of information from one or multiple different sensors. For example, some embodiments include simultaneous analysis of signals from an activity sensor (G-sensor, accelerometer) and from a physiological sensor (MV sensor, ventilation minute), with, as appropriate, activity/rest dissociated analysis, so as to create a number of specific indexes that may reveal a worsening of the clinical condition of the patient. If necessary, early warning of heart failure may be triggered when a number of these indexes respond to a battery of predefined criteria. They may also provide, in addition to the analysis of the clinical condition of the patient from information from the MV and G sensors, an evaluation of the cardiac contractility from a endocardial acceleration (EA) or a cardiac bioimpedance signal. Respective analysis methods may produce each one warning signal of cardiac decompensation. A cross-analysis may deliver a preventive alert composite signal, at different levels, depending on the occurrence of the alarm signals generated by these two methods.

EP 1767244 A1, EP 1790382 A1, and EP 1867360 A2 and their U.S. counterparts, U.S. Patent Application Publications US2007/0073350, US2007/0150016, and US 2007/0293736, respectively, are incorporated herein by reference in their entireties. They provide more information related to such methods.

Various other embodiments include preventative diagnostic techniques of cardiac decompesation, based on changes in trends in medium and long term of respiratory frequencies and thoracic impedance. The WO 2011/005376 A1 and U.S. Patent Application Publication 2011/0166472 A1 are incorporated herein by reference in their entireties. They provide more information related to some such exemplary techniques, according to some embodiments.

Devices according to various embodiments may be used for remote monitoring. For example, the patient may daily connect a first device through a wireless connection to a second device, which may itself be connected to a remote site. The first device may transmits the collected signals generated by the implant since the last connection.

Existing cardiac decompensation prevention methods generate a significant number of false alarms, usually false positives. These false positives would be of no interest to the physician, but may unnecessarily worry the patient. Setting of different criteria for triggering an alert may be chosen so as to increase the triggering sensitivity of the alarm by adjusting various fixed parameters (thresholds), incremental parameters (minimum or maximum percentages of increase), or metarules analyzing the evolution of the indexes and of their combination over several days.

Indeed, the sensitivity and specificity (that is to say, the selectivity of the analysis) may be regarded as two antagonistic notions, to the extent that an increase in sensitivity may be accompanied by a lower specificity with a corresponding increase in the risk of false alarms. Conversely, if the alert criteria are rendered stricter, this may reduce the false positive cases, but with the risk of not triggering alerts in critical cases.

The consequences of false alarms may be even more important when the device not only delivers an alert (diagnostic function), but also modifies its operation to match with the assumed improvement or worsening of the situation of the patient, including reprogramming of some of its functions.

EP 0966987 A1 and its U.S. counterpart: U.S. Pat. No. 6,246,910 are incorporated herein by reference in their entireties. They describe a rate-response device, such as a device heart rate-responsive pacemaker, defibrillator, and/or cardiovertor, or the like.

EP 0570896 A2 is incorporated herein by reference in its entirety. It discloses an exemplary technique for discriminating between tachycardias by comparing feature value(s) of a heart-related signal that are non-baseline with feature value(s) of a heart-related signal that are normal baseline.

U.S. Pat. No. 7,570,990 is incorporated herein by reference in its entirety. It discloses generating an atrial flutter suspicion signal.

Other techniques regarding model-cycles are disclosed in WO2006/105143 A1 and WO2011/005376 A1, which are incorporated herein by reference in their entireties.

The aim of the invention, according to various embodiments, is to provide a cardiac decompensation preventive diagnosis technique which increases the specificity of detection methods (that is to say, generates much less false alerts), but without altering their sensitivity. The aim of the invention is also to disclose such a method which, for its implementation, is not very demanding in terms of hardware (such as the processor(s) or memory) and software (such as the software's complexity or computation time) resources. This is so it may be used within an implant, with hardware and/or software and with no significant impact on the energy balance, including the activity of the processor, which has a direct impact on power consumption and consequently on the autonomy of the implant.

The starting point of the invention lies in the observation that the information contained in the electrogram (EGM) signals in the heart sounds, translated by the endocardial acceleration (EA), or in the episodes of stress/recovery is insufficiently exploited for preventive diagnosis of congestive heart failure. This is primarily because the analysis of this information according to previously known techniques requires relatively high computational and memory resources.

The basic idea of the invention is to discriminate between a situation that is called "in-suspicion" situation (positive response of the diagnostic method) and an "off-suspicion" situation (otherwise), without triggering an alarm at this stage. Triggering an alarm at this stage inappropriately may be undesirable because the result may be too unreliable.

The "in-suspicion" or "off-suspicion" marker may be used to describe and/or store a template or "model-cycle." A model-cycle may includes at least one piece of information of relatively complex nature of the type mentioned above, for example a complete EGM or EA cardiac beat, optionally averaged, so a complete waveform.

The device may store (or update) such an "in-suspicion" model-cycle and/or an "off-suspicion" model-cycle. The device may then compare the two model-cycles in order to characterize their differences. Their differences may be used for deriving one or more indicators representative of the differences.

From this (these) indicator(s), reflecting the difference between the two in-suspicion/off-suspicion model-cycles, the cardiac decompensation preventive alert may be triggered (or not).

More particularly, the specificity of this alert may be much better than that which could be obtained with previously known techniques.

Moreover, the performed analysis may only compare two model-cycles that have been stored, which in itself may be done in a relatively simple and efficient method. It may be done without continuously analyzing the original data (EGM, EA, or the like) used to form the model-cycle. Such an analysis that would have required much more important computing resources.

The memory consumption may be very low in preferred embodiments. In some such embodiments, the device stores, for later comparison: (a) an "off-suspicion" EGM beat and an "in-suspicion" EGM beat, and/or (b) an "off-suspicion" EA beat and an "in-suspicion" EA beat, and/or (c) parameters collected during an "off-suspicion" episode of stress/recovery and during a similar "in-suspicion" episode of stress/recovery, for example, the recording of a cycle describing the minute ventilation as a function of heart rate in each of these situations.

Another advantage of the invention may be the ability to use morphological indicators to compare model-cycles, such as intercorrelation measurements. These measurements, for the purpose of the diagnosis of heart failure, may be more powerful indicators than standard indicators (indicators simply resulting from a comparison of data points such as the R-wave amplitude, amplitude of the peak of endocardial acceleration, etc.). This may allow a further increase in the specificity of the detection method.

The invention may include a device, such as a device as described by EP0570896 A2, above. Such a device may include a processor configured for data collection of cardiac activity; production of at least one regular index of the patient's clinical condition, and generation of an early warning of cardiac decompensation according to said at least one index of the patient's clinical condition; and collection of reference episodes. These episodes may include signals of electrical activity of the myocardium, hemodynamic activity signals of the myocardium, and/or indicators reflecting the variation of the activity and/or hemodynamic physical parameters between phases of effort and phases of recovery. In various embodiments, the processor may be further configured for discrimination of analysis of such events according to predefined criteria to assign each of these episodes a cardiac decompensation in-suspicion or out-of-suspicion marker. In various embodiments, the processor is further configured for processing and, optionally, storage, of model-cycles. This processing may result in the production from the episodes at least two model-cycles from episodes collected in the respective cardiac decompensation in-suspicion and off-suspicion situations. In various embodiments, the processor is further configured for characterization of a difference between an in-suspicion model-cycle and an off-suspicion model-cycle. This characterization may be used for production of the at least one index of the patient's clinical condition.

The model-cycle may include at least one endocardial electrogram beat recorded during an episode that meets the predetermined conditions of heart rate and activity of the patient. The model-cycle may include at least one endocardial acceleration signal beat recorded during an episode that meets the predetermined conditions of heart rate and patient activity. The model-cycle may include at least one minute ventilation vs. heart rate characteristic pattern recorded during an episode comprising a phase of stress followed by a phase of recovery of the patient.

In various embodiments, the device includes a processor configured to update the model-cycles. Each model-cycle may be defined as a combination of the last model-cycle produced with at least one model-cycle previously produced.

An analysis module may advantageously calculate an index of clinical condition from a plurality of averaged earlier model-cycles.

FIG. 1 illustrates in block diagrams one embodiment, in which the interweaving of the different processing modules may lead to the delivery (or not) of an early warning of cardiac decompensation (HF, Heart Failure).

A method 10, that is herein referred to as the "original method," analyzes standard data of cardiac activity 12, such as activity level, respiratory rate, and/or heart rate, etc. These may be registered day to day.

This method 10 may be used to deliver (or not) a warning of cardiac decompensation (HF). However, in various embodiments the result of the analysis is not a warning indicator, but only an intermediate marker to discriminate between a situation that is considered "in suspicion of cardiac decompensation" (ES) or otherwise, "off-suspicion of cardiac decompensation" (HS). The assignment of this HS or ES marker is symbolized by the block "Off-suspicion/In-suspicion switch."

A number of relatively complex and information-rich data may also be collected by the device (block 14). These data may include signals of electrical activity of the myocardium, including endocardial EGM. Thus, the data may include signals of hemodynamic activity, such as an endocardial acceleration signal (EA) or a cardiac bioimpedance signal. The data may include signals reflecting changes in various parameters (heart rate, ventilatory frequency and amplitude, activity, etc.) during an alternation of stress phase and recovery phase. Alternatively, these data may include any combination of the above options.

These data may be stored as a "model-cycle." In some embodiments, a model-cycle is stored after daily averaging or other update preprocessing. It may be stored as an "in-suspicion" model-cycle (block 16) or as a "off-suspicion" model-cycle (block 18), based on the suspicion marker ("Out-of-suspicion/in suspicion" switch) when the input data is collected.

A processor may later compare the two model-cycles stored 16 and 18 (block 20). This may allow the processor to characterize the difference between these two model-cycles as in-suspicion or as off-suspicion. In some preferred embodiments, this comparison may be carried out, as described below, with reference to FIG. 11, when the "in-suspicion" model-cycle is updated, for at this time one alert may potentially be triggered.

One or more indexes of the clinical status of the patient may be produced according to predetermined criteria. An index may then be analyzed (block 22), using a processor, to detect a situation of potential cardiac decompensation (block 22). If potential cardiac decompensation is detected, a corresponding alert may be delivered, using a processor.

FIG. 2 shows a first example, according to one embodiment, of input data collected by the block 14. In this case, an EGM signal may be collected on the duration of a heartbeat 24, for example, using an implantable device. For instance, a unipolar signal may be recorded under predetermined conditions. Sample predetermined conditions may include: at rest, during the night, at a constant heart rate, etc. The device may record such a model-cycle 24 in a off-suspicion situation, and another model-cycle 24 in a in-suspicion situation.

FIG. 3 shows a second example of input data collected by the block 14, according to one embodiment. In this case, an EA signal is collected, for example, using an implantable device. The collection may take place under predetermined conditions on the duration of a heartbeat 26. The device may record such a model-cycle 26 in a off-suspicion situation, and another model-cycle 26 in a in-suspicion situation.

FIG. 4 shows a third example of input data collected by the block 14, according to one embodiment. In this case, a cycle 28 gives the variation of minute ventilation (MV) according to the heart rate (HR). This cycle may be stored during a stress phase followed by a recovery phase. The described loop thus may include a portion 32 corresponding to the start of the stress phase, followed by a portion 32 corresponding to the recovery phase after stopping this effort. The loop may also include an unregistered portion 34 for which the recording triggering indicators (minimum effort, minimum level of activity, ventilation, etc.) may not be achieved yet. This may be unlike the parties 30 and 32 which, however, correspond to a situation such that these triggering indicators were achieved. This may confirm that recording the stress/recovery cycle is relevant.

Below is a more detailed description of the implementation of the various steps of the method, according to various embodiments.

FIG. 5 illustrates a general chronology of the method of the invention, according to one embodiment.

In FIG. 5, the first phase (block 36), performed by the data collection module 1 (block 14 in FIG. 1), is to wait for an episode that is recognized as valid. That is, it corresponds to a certain number of predetermined conditions: stable heart rate, patient in rest state, no arrhythmia, or the like, or any combination of those. If the episode is considered valid (block 38), a classification may be made on the basis of in-suspicion/off-suspicion marker/(block 40) delivered by the Module #2 of data analysis (block 10 of FIG. 1).

The corresponding "in-suspicion" model-cycle (block 42) or "off-suspicion" model-cycle (block 44) may be stored (or updated). This step may correspond to Module #3 in FIG. 1 (blocks 16, 18).

The next step (block 46) may include comparing the two off-suspicion and in-suspicion model-cycles to characterize their differences. This characterization may be used to extract one or more indicators based on the comparison (module #4, block 20 in FIG. 1).

These various indicators may then be processed (block 48) by a second cardiac decompensation diagnosis method, so as to provide a final, specific, alert, of risk of cardiac decompensation in the short term (Module #5, block 22 in FIG. 1).

Figure 6:
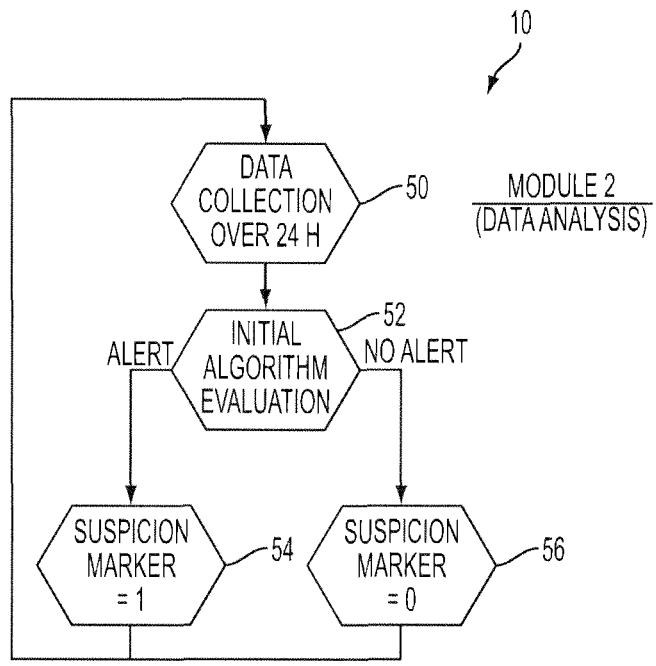
FIG. 6 is a flowchart illustrating analysis of input data and their classification by assigning an in-suspicion or off-suspicion marker, according to an exemplary embodiment.

FIG. 6 illustrates the steps of Module #2 for the purpose of analysis of the daily recorded standard data of cardiac activity 12, according to one embodiment. The analysis may be to establish the "off-suspicion" or "in-suspicion" category of the period during which the data may be collected for the creation of the model-cycles.

The data in question (level of activity, respiration rate, heart rate, etc.) may be collected, for example, over a 24-hour period (block 50). The data may then be assessed (block 52) by the original method. If the result of this analysis is "triggering of an alert", then an "in-suspicion" marker may be placed (block 54). Otherwise, the marker may be set to "off-suspicion" (block 56).

Figure 7:
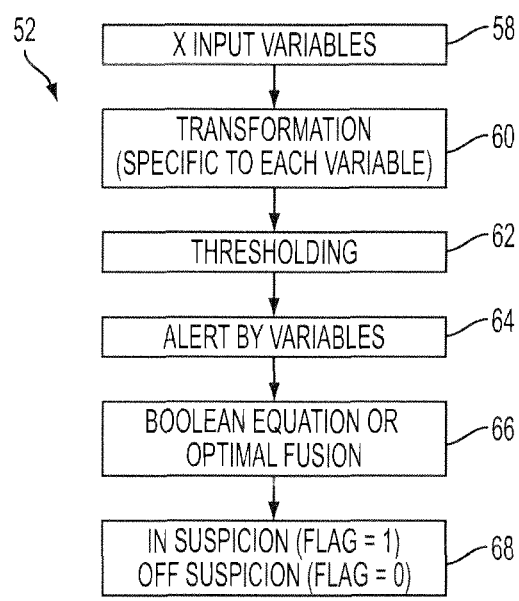
FIG. 7 is a flowchart illustrating a method of cardiac decompensation detection allowing discrimination of off-suspicion and in-suspicion states, according to an exemplary embodiment.

FIG. 7 shows an example of method 52, according to one embodiment. This method may be any known method generating cardiac decompensation prediction alerts based on daily data, such as a method described in EP 1867360 A2 or WO 2011/005373 A1, above, for example.

A number of input variables may be collected (block 58). These may include, transthoracic impedance, duration of the respiratory period, heart rate, activity duration, rate of premature ventricular contractions, or the like, or any combination of those.

These various variables may be transformed and weighted (block 60), with a peculiar sensitivity and specificity to each of these variables or to a combination thereof (e.g. the number of respiratory cycles in which the impedance is below a given threshold, etc.).

Thresholds may be applied (block 62), leading to specific alerts for each variable (block 64). These alerts may then be combined together (block 66) to produce a global alert. In various embodiments, a global alert may be a marker of in-suspicion situation (block 68), or otherwise, as a marker of off-suspicion situation.

Figure 8A:
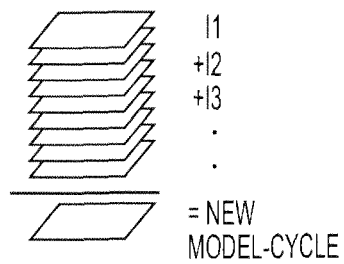
FIG. 8a is an illustration of a technique for update of stored model-cycles, according to an exemplary embodiment.
Figure 8B:
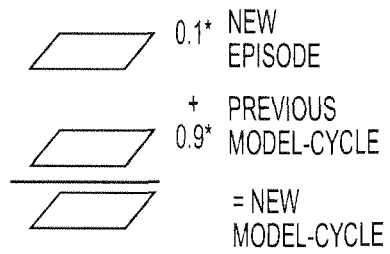
FIG. 8b is an illustration of another technique for update of stored model-cycles, according to an exemplary embodiment.

FIGS. 8a and 8b show two examples of management of the update of the model-cycles (in-suspicion- or off-suspicion), performed by Module #3 in FIG. 1, according to some embodiments.

As shown in FIG. 8a, a technique of "update with oblivion" which requires keeping n temporary records of the data may be used, for example, the new recording replacing the oldest received temporary recorded model-cycle and the finally stored model-cycle being the average of the n temporary records. If a noisy episode is collected, the impact of it may be reduced due to the averaging. It may eventually disappear from the stored records and may no longer affect the averaged model-cycle.

FIG. 8b illustrates another "exponential recording" technique, which may require recording of the last data collected, giving it a weight (e.g. 10%) compared to the average of the n records previously collected and averaged, affected by a (e.g. 90%) weighting. Significant noise or measurement error may have an impact on the useful model-cycle for a longer period. Conversely, the amount of memory required may be much lower than in the previous case.

The data used to build averaged model-cycles preferably are as reliable as possible. Preferably, they would be recorded under comparable conditions. In some embodiments, the absence of noise is verified. In some embodiments, the conditions during recording of these data are constant over time.

To detect a risk of cardiac decompensation, the data during a long enough "off-suspicion" period may be analyzed. This may establish a model-cycle that represents, for example, the last ten days, with a daily cycle. In some preferred embodiments, this model-cycle is an "off decompensation" state. But if decompensation begins to appear, it may "pollute" the last few days of this period (during the period necessary to the initial method to start proving the suspicion). In contrast, for a in-suspicion model-cycle, a shorter resolution, preferably 3 to 6 hours, may be required to have a minimum amount of time for a sufficient number of cycles recorded to provide a quick "in-suspicion" model-cycle. This is to make fast the comparison with the "off-suspicion" model-cycle already stored and averaged. This resolution of 3 to 6 hours is a compromise between a shorter resolution, which may imply a high computation time; and, vice-versa, too low a resolution that may limit the early detection of risk of decompensation. However, if it is desirable that the update of the model-cycles is conducted under really similar conditions, it may be possible to wait a period of sleep (for data including EGM or EA beats).

If the input data is a effort/recovery cycle and not an EGM or EA beat, an "effort" may be defined as an episode characterized by the crossing of activity, ventilation, and/or heart rate thresholds, and minimum duration, for example, a duration of effort more than or equal to 2 minutes. An episode of effort/recovery may be taken into account if it occurs at least one hour after the previous validated episode. This time period may be lower than the expected latency for the recording of the EGM or EA beats (such as 3 hours), because the episodes of effort/recovery may be highly variable. If a reliable model-cycle is desired, a greater number of episodes may be required.

Figure 9:
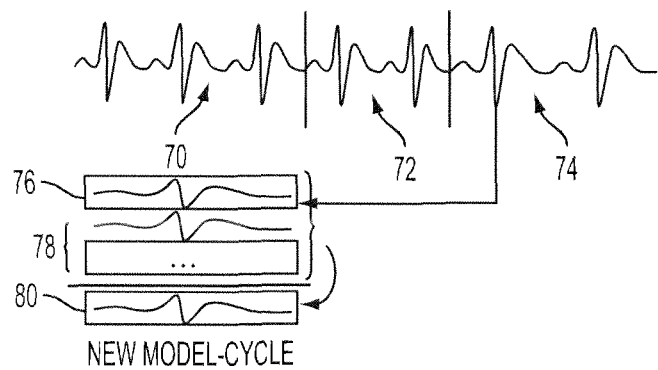
FIG. 9 is an illustration of a method for the selection of EGM or EA beats that are used to create the averaged model-cycle according to one or the other of the techniques shown in FIGS. 8a and 8b, according to an exemplary embodiment.

FIG. 9 schematically illustrates the method of selection of the EGM or EA beats, according to one embodiment. The EGM or EA beats may be used to create the averaged model-cycle according to one or the other of the techniques, such as those shown in FIGS. 8a and 8b.

In FIG. 9, there is schematically shown at 70, 72, 74 . . . , a succession of beats, for which the expiry of a period of at least 3 hours since the last registration of a beat may be waited for in any event. For example, if a beat in nocturnal conditions is desired, a period of 24 hours may be used. Once this period has elapsed, the first beat fulfilling, for instance, the following conditions, may be taken into account. A condition may include that a heart rate be between the base frequency and the base frequency+10 bpm (thus the beat 72, may be too fast, and not considered). A condition may include that a beat corresponds to a ventricular spontaneous depolarization. A condition may include a lack of effort (for example, if the activity sensors are available). A condition may include a signal/noise ratio, for example, greater than 40 dB, to eliminate too-noisy episodes.

If these conditions are met, for example, for the beat 74, it may be recorded (as in 76), possibly after temporal shifting compared to the previously stored beats (as in 78). The new updated model-cycle 80 is then calculated by the methods described above in connection with FIGS. 8a and 8b, that is to say, averaging with oblivion or exponential averaging.

The extraction of the indicators based on the comparison of the two in-suspicion and off-suspicion model-cycles (operated by Module #4, block 20 of FIG. 1) may be performed. This may be done according to various methods, depending on the type of data for the model-cycle. For example, a model-cycle may include an EGM beat, the following indicators may be extracted: difference in amplitude of the R wave between the off-suspicion beat and the in-suspicion beat; difference in QRS duration; difference in PR interval; occurrence of VV desynchronization; morphological indicator for comparing two beats EGM, such as Euclidean distance, Dynamic Time Warping (DTW), calculation of a cross-correlation, geometric descriptor such as the norm of the tangent vector (both techniques are explained in EP 2324885 A1 (counterpart: US2011/0118804) to SORIN CRM, within a capture test), or the like.

When the model-cycle is constituted by an EA wave, for example, a model-cycle may include an amplitude difference between the first peak of endocardial acceleration PEA1 and/or the second peak PEA2; a morphological indicator such as Euclidean distance after temporal shifting of the two waves, Dynamic Time Warping, intercorrelation, or the like.

In the case, the model-cycle is a minute ventilation versus cardiac rhythm curve, for example, a model-cycle may include a comparison of the areas under the curves; comparison of maxima of the MV/HR ratios; direct comparison of the total number of samples in the off-suspicion and in-suspicion histograms, or the like.

Figure 10:
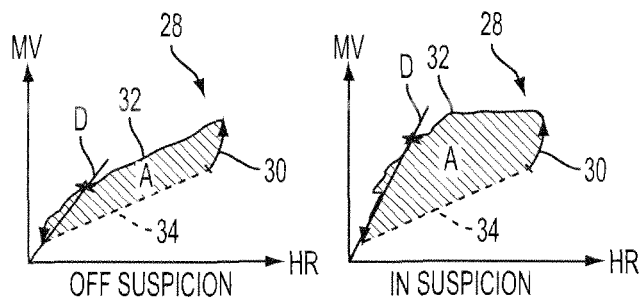
FIG. 10 is a diagram of two examples of indicators to describe the difference between in-suspicion and out-of-suspicion situations of a model-cycle corresponding to the trace of the minute ventilation (MV) as a function of heart rate (HR) during a recovery phase following a stress phase, according to an exemplary embodiment.

FIG. 10 in particular illustrates these parameters, according to one embodiment. FIG. 10 shows that in the "in-suspicion" situation, the area (A) is larger. So is the maximum MV/HR, parameter represented by the slope of the line D. The area may be easily evaluated, especially after scanning of the samples by a simple summation. The simple summation may be performed with extremely small computational resources and very quickly.

The alert may be the final result of the analysis carried out by the detection method module #5.

This method may weight the different indicators resulting from the comparison of the two in-suspicion and off suspicion model-cycles (indicators produced by the module #4). This may optionally and advantageously be combined with indicators also delivered by the initial detection method (in the Module #2).

The indicators resulting from the comparison of the two on/off-suspicion model-cycles may be, for example: alert if the correlation of the in/off-suspicion EGM beats is less than 0.8; alert if the correlation between In/off-suspicion EA beats is less than 0.6; alert if the average difference between the two in/off-suspicion stress/recovery histogram curves is greater than 10%; or the like.

The indicators given by the original method may be, for example: alert if the measured impedance decreases of 200 ohms over 20 days; warning if the measured respiratory period decreases from 1.5 seconds over 10 days; alert if the number of disturbed breaths increases of 1000 over 20 days; warning if the measured heart rate increased by 15 bpm to 20 days; alert if the activity time decreases by at least 1 hour over 20 days; alert if the number of extrasystoles increased of 1000 over 20 days; or the like.

These alerts may be each combined and weighted by a factor, to deliver a single, overall alert. The respective weights may be chosen according to the sensitivity and specificity of each alert, evaluated on a reference clinical database.

Figure 11:
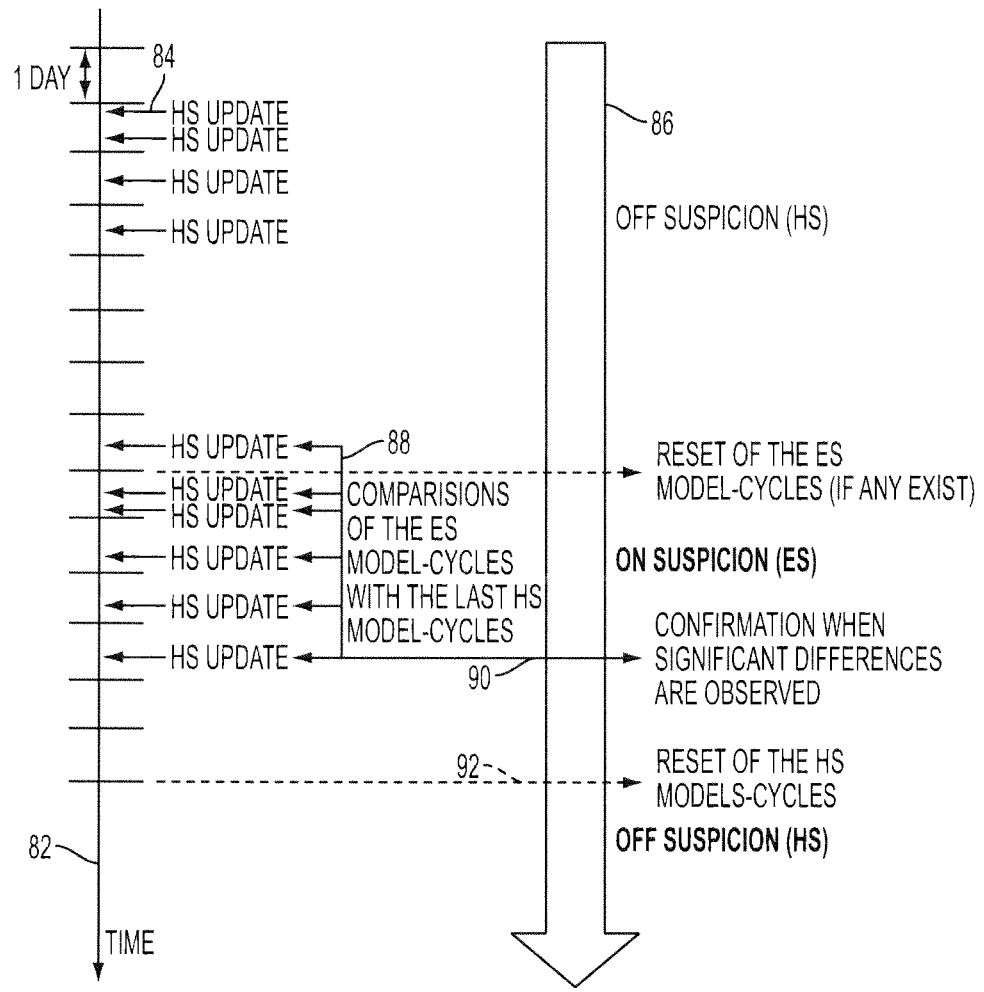
FIG. 11 is a diagram that illustrates a succession of different markers and indexes over a period of several days, according to an exemplary embodiment.

FIG. 11 is an example of a sequence of results of implementation of the technique of the invention over a period of several days, according to one embodiment.

The time axis 82 indicates, day after day, updates of the model-cycles, schematized by arrows 84. Each update may correspond to a new validated episode.

These updates (MAJ) may be located in an off-suspicion state (HS), or in an in-suspicion state (ES), shown in timeline 86.

The step of comparison of the model-cycles, diagrammed by the double arrows 88, may executed as soon as it is possible to store at least one off-suspicion model-cycle and at least one in-suspicion model-cycle. The comparison may be performed at each update of an "in-suspicion" model-cycle. This may be because it is at that moment that an alert may potentially be triggered.

This comparison may be repeated at each update of an in-suspicion model-cycle (new episode enabled). When the differences between off-suspicion/in-suspicion model-cycles are too high, then an alert may be delivered, as in 90.

When the situation returns to an "off-suspicion" state, then the off-suspicion model-cycle may be reset (as in 92), until the next off-suspicion valid episode. At that time, this cycle model may be stored again for later use.

What is claimed is:

1. A method of diagnosis of heart failure, the method comprising:

collecting, using an implantable device, a plurality of reference episodes, the reference episodes comprising at least one of: electrical activity signals of a myocardium; myocardium hemodynamic activity signals, or indicators reflecting variation of parameters between phases of effort and phases of recovery, wherein the parameters comprise at least one of physical parameters, activity parameters, or hemodynamic phase parameters between phases of effort and phases of recovery;

analysing, using the implantable device, the plurality of reference episodes based on predefined criteria to assign each of the reference episodes an in-suspicion marker or an off-suspicion marker, wherein the in-suspicion marker indicates a suspicion that the reference episode is associated with cardiac decompensation, wherein the off-suspicion marker indicates a suspicion that the reference episode is not associated with cardiac decompensation, and wherein the reference episodes assigned the in-suspicion marker and the reference episodes assigned the off-suspicion marker are interspersed within the plurality of reference episodes;

generating, using the implantable device, an in-suspicion model-cycle based on data associated with a plurality of in-suspicion reference episodes to which the in-suspicion marker has been assigned;

generating, using the implantable device, an off-suspicion model-cycle based on data associated with a plurality of off-suspicion reference episodes to which the off-suspicion marker has been assigned; and determining, using the implantable device, whether to generate an early heart failure alert based on a difference between the in-suspicion model-cycle and the off-suspicion model-cycle.

2. The method of claim 1, wherein the in-suspicion model-cycle or off-suspicion model-cycle comprises at least one endocardial electrogram beat recorded during an episode fulfilling predetermined conditions of heart rate and patient activity.

3. The method of claim 1, wherein the in-suspicion model-cycle or off-suspicion model-cycle comprises at least one beat of an endocardiac acceleration signal recorded during an episode fulfilling predetermined conditions of heart rate and patient activity.

4. The method of claim 1, wherein the in-suspicion model-cycle or off-suspicion model-cycle comprises at least one minute ventilation versus heart-rate characteristic pattern that was recorded during an episode comprising an effort phase followed by a recovery phase of the patient.

5. The method of claim 1, further comprising:
updating the in-suspicion model-cycle and off-suspicion model-cycle; and
storing the updated in-suspicion model-cycle and updated off-suspicion model-cycle.

6. The method of claim 5, wherein each of the in-suspicion model-cycle and the off-suspicion model-cycle is a combination of a previous model-cycle with at least one older model-cycle.

7. The method of claim 1, wherein generating the early heart failure alert comprises:
generating at least one index of a clinical condition of a patient, based on the difference between the in-suspicion model-cycle and the off-suspicion model-cycle; and
generating an early heart failure alert based on the at least one index.

8. The method of claim 7, wherein the at least one index of a clinical condition is updated periodically.

9. The method of claim 7, wherein the at least one index is calculated based on an average of model-cycles.

10. A device for the diagnosis of heart failure, comprising:
a processor, configured to:
collect data relating to a plurality of reference episodes, the reference episodes comprising at least one of: electrical activity signals of a myocardium; myocardium hemodynamic activity signals, or indicators reflecting variation of parameters between phases of effort and phases of recovery, wherein the parameters comprise at least one of physical parameters, activity parameters, or hemodynamic phase parameters between phases of effort and phases of recovery;

analyze the plurality of reference episodes based on predefined criteria to assign each of the reference episodes an in-suspicion marker or an off-suspicion marker, wherein the in-suspicion marker indicates a suspicion that the reference episode is associated with cardiac decompensation, wherein the off-suspicion marker indicates a suspicion that the reference episode is not associated with cardiac decompensation, and wherein the reference episodes assigned the in-suspicion marker and the reference episodes assigned the off-suspicion marker are interspersed within the plurality of reference episodes;

generate an in-suspicion model-cycle based on data associated with a plurality of in-suspicion reference episodes to which the in-suspicion marker has been assigned;

generate an off-suspicion model-cycle based on data associated with a plurality of off-suspicion reference episodes to which the off-suspicion marker has been assigned; and determine whether to generate an early heart failure alert based on a difference between the in-suspicion model-cycle and the off-suspicion model-cycle.

11. The device of claim 10, wherein the in-suspicion model-cycle or off-suspicion model-cycle comprises at least one endocardial electrogram beat recorded during an episode fulfilling predetermined conditions of heart rate and patient activity.

12. The device of claim 10, wherein the in-suspicion model-cycle or off-suspicion model-cycle comprises at least one beat of an endocardiac acceleration signal recorded during an episode fulfilling predetermined conditions of heart rate and patient activity.

13. The device of claim 10, wherein the in-suspicion model-cycle or off-suspicion model-cycle comprises at least one minute ventilation versus heart-rate characteristic pattern that was recorded during an episode comprising an effort phase followed by a recovery phase of the patient.

14. The device of claim 10, further comprising:
a memory;
wherein the processor is further configured to:
update the in-suspicion model-cycle and off-suspicion model-cycle; and
store, in the memory, the updated in-suspicion model-cycle and updated off-suspicion model-cycle.

15. The device of claim 14, wherein each of the in-suspicion model-cycle and the off-suspicion model-cycle is a combination of a previous model-cycle with at least one older model-cycle.

16. The device of claim 10, wherein generating the early heart failure alert comprises:
generating at least one index of a clinical condition of a patient, based on the difference between the in-suspicion model-cycle and the off-suspicion model-cycle; and generating an early heart failure alert based on the at least one index.

17. The device of claim 16, wherein the at least one index of a clinical condition is updated periodically.

18. The device of claim 16, wherein the at least one index is calculated based on an average of model-cycles.

19. The device of claim 10, wherein the device is a pacing, resynchronization, or defibrillation device or an implant for diagnostic purposes.

20. A processor-readable, non-transitory storage medium having instructions stored thereon that, when executed by a processor, cause the processor to:
    collect data relating to a plurality of reference episodes, the reference episodes comprising at least one of: electrical activity signals of a myocardium; myocardium hemodynamic activity signals, or indicators reflecting variation of parameters between phases of effort and phases of recovery, wherein the parameters comprise at least one of physical parameters, activity parameters, or hemodynamic phase parameters between phases of effort and phases of recovery;
    analyze the plurality of reference episodes based on predefined criteria to assign each of the reference episodes an in-suspicion marker or an off-suspicion marker, wherein the in-suspicion marker indicates a suspicion that the reference episode is associated with cardiac decompensation, and wherein the off-suspicion marker indicates a suspicion that the reference episode is not associated with cardiac decompensation, and wherein the reference episodes assigned the in-suspicion marker and the reference episodes assigned the off-suspicion marker are interspersed within the plurality of reference episodes;
    generate an in-suspicion model-cycle based on data associated with a plurality of in-suspicion reference episodes to which the in-suspicion marker has been assigned;
    generate an off-suspicion model-cycle based on data associated with a plurality of off-suspicion reference episodes to which the off-suspicion marker has been assigned; and
    determine whether to generate an early heart failure alert, based on a difference between the in-suspicion model-cycle and the off-suspicion model-cycle.

* * * * *